United States Patent [19]

Marvel et al.

[11] Patent Number: 4,499,258

[45] Date of Patent: Feb. 19, 1985

[54] POLYAROMATIC ETHER-SULFONE-KEYTONES WITH FLUORO-SUBSTITUTED-P-CYCLOPHANE UNITS AS CROSS-LINKING SITES

[75] Inventors: Carl S. Marvel, Tucson, Ariz.; See Lin, Taipei, Taiwan

[73] Assignee: The United States of America as represented by the Secretary of the Air Force, Washington, D.C.

[21] Appl. No.: 615,507

[22] Filed: May 30, 1984

Related U.S. Application Data

[62] Division of Ser. No. 552,552, Nov. 16, 1983, Pat. No. 4,476,062.

[51] Int. Cl.$^3$ .............................................. C08G 75/20
[52] U.S. Cl. .................................... 528/173; 528/190; 528/191; 528/193; 528/194
[58] Field of Search ............... 528/172, 190, 191, 193, 528/194; 260/544 B

[56] References Cited

U.S. PATENT DOCUMENTS 3,491,142  1/1970  Yeh et al. ....................... 260/544 B
3,754,015  8/1973  Hedaya ........................... 260/544 B

*Primary Examiner*—Lester L. Lee
*Attorney, Agent, or Firm*—Donald J. Singer; William J. O'Brien

[57] ABSTRACT

Polyaromatic ether-sulfone-ketones containing fluoro-substituted-p-cyclophane units were prepared from isophthaloyl chloride, terephthaloyl chloride, diphenyl ether, diphenoxydiphenyl sulfone and a small amount of either 1,1, 2,2, 9,9, 10,10-octafluoro [2,2]-p-cyclophane (type B) or pseudo-p-1,1, 2,2, 9,9, 10,10-octofluoro [2,2]-p-cyclophane bis-acid chloride (type A) by a Friedal-Crafts type polymerization procedure. The p-cyclophane units were incorporated as cross-linking sites.

4 Claims, No Drawings

POLYAROMATIC ETHER-SULFONE-KEYTONES WITH FLUORO-SUBSTITUTED-P-CYCLOPHANE UNITS AS CROSS-LINKING SITES

STATEMENT OF GOVERNMENT INTEREST

The invention described herein may be manufactured and used by or for the Government for governmental purposes without the payment of any royalty thereon.

This is a division of application Ser. No. 552,552, filed Nov. 16, 1983, now U.S. Pat. No. 4,476,062.

BACKGROUND OF THE INVENTION

This invention relates to a novel monomeric and polymeric compounds and to methods for their preparation. In a more specific aspect, this invention relates to polyaromatic ether-sulfone-ketones with fluorinated-p-cyclophane units as cross-linking sites and to a novel fluoronated-p-cyclophane bis-acid fluoride monomer utilized in the preparation of the polyaromatic ether-sulfone-ketones.

In order to prepare thermally stable laminating resins, recent research efforts have concentrated on developing new processes for the cross-linking of resins without liberating undersirable gaseous side products. The synthesis of linear polymers incorporating internal p-cyclophane units and the cross-linking of these polymers by heating above 250° C. has been accomplished heretofore by Myers et al al as reported in R. Z. Myers, J. W. Hamersma and H. S. Green, J. Polym. Sci., B, 10, 685 (1972).

Cross-linking in such polymers is effected by thermal homolysis of the dimethylene bridge in the highly strained p-cyclophane system to form 4,4'-ethylenedibenzyl diradicals (II). In the absence of free radical traps, these radicals may either recombine intramolecularly to regenerate (I), or may react intermolecularly acorss polymer chains to give rise to ethylenic cross-links.

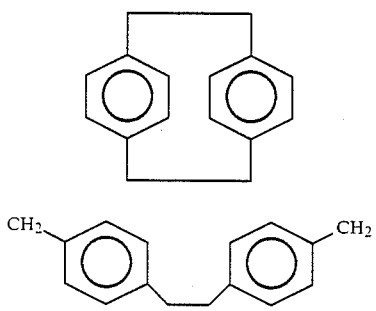

I

II

Earlier publications, such as K. P. Sivaramakrishnan, C. Samyn, I. J. Westerman, D. T. Wong and C. S. Marvel, J. Polym. Sci., Polym. Chem. Ed., 13, 2507 (1975), have disclosed that some dozen polymers containing p-cyclophane were prepared and were thermally stable laminates. As early as 1933, the unusual properties of polytetrafluoroethylene (Teflon) were observed and the interest in the synthesis of polymers fluorine increased greatly thereafter.

As a consequence, a considerable research effort has been generated in an attempt to provide new and useful fluoro-substituted polymers. The results of that research effort have culminated in the development of a novel monomeric acid chloride as well as the preparation of novel polymeric compounds resulting from the use of that novel monomer as a cross-linking site. Instead of using simple-p-cyclophane units, the present invention unexpectedly discovered that two fluorine substituted p-cyclophanes, one of which is novel, could be incorporated as cross-linking sites along the polymer chain. The resulting polymers are excellent film-formers and, in addition, form excellent glass fiber laminates characterized by excellent thermal stability.

SUMMARY OF THE INVENTION

The present invention concerns itself with the preparation of a novel fluoro-substituted-p-cyclophane bis-acid chloride monomer. It also involves the preparation of two types of polyaromatic ether-sulfone-ketones containing fluoro-substituted-p-cyclophane units. These two types of polymers, type A and type B, were prepared from isophthaloyl chloride, terephthaloyl chloride, dipenyl ether, diphenoxydiphenyl sulfone and a small amount of either 1,1, 2,2, 9,9, 10,10-octafluoro [2,2]-p-cyclophane (type A) or pseudo-p-1,1, 2,2, 9,9, 10,10-octofluoro [2]-p-cyclophane bis-acid chloride (type B) by Friedel-Crafts type polymerization.

The p-cyclophane units were incorporated as cross-linking sites. Cross-linking was achieved by curing the polymers at 300°–350° C. for several days. The resulting polymers contained 1–10 wt. % fluoro-substituted p-cyclophane units and were moderately soluble in dichloromethane, DMF and sulfuric acid with inherent viscositites between 0.4 and 0.6. Laminates on glass fibere were made with excellent thermal stability.

Accordingly, the primary object of this invention is to provide novel polyaromatic ether-sulfone-ketones containing fluro-substituted p-cyclophane units along the polymer chain.

Another object of this invention is to provide curable polymeric materials that do not produce undesireable gaseous side-products when subjected to cross-linking or curing procedures.

Still another object of this invention is to develop a novel monomeric fluoro-substituted-p-cyclophane bis acid chloride useful in the preparation of novel polyaromatic ether-sulfone-ketones.

A further object of this invention is to provide novel polymeric materials that are especially useful as laminating resins possessing excellent thermal stability.

The above and still further objects and advantages of the present invetion will become more readily apparent upon consideration of the following detailed description thereof.

DESCRIPTION OF THE PREFERRED EMBODIMENT

In accordance with this invention, it has been found that the objects of this invention can be accomplished through the synthesis of a novel fluoro-substituted p-cyclophane bis acid chloride monomer and its resulting polymerization through a Friedal-Crafts type polymerization procedure to produce novel polyaromatic ether-sulfone-ketones having fluro-substituted-p-cyclophane units as cross-linking sites.

The two fluorine substituted p-cyclophanes utilized in this invention are illustrated by the following structural formulas (III and IV):

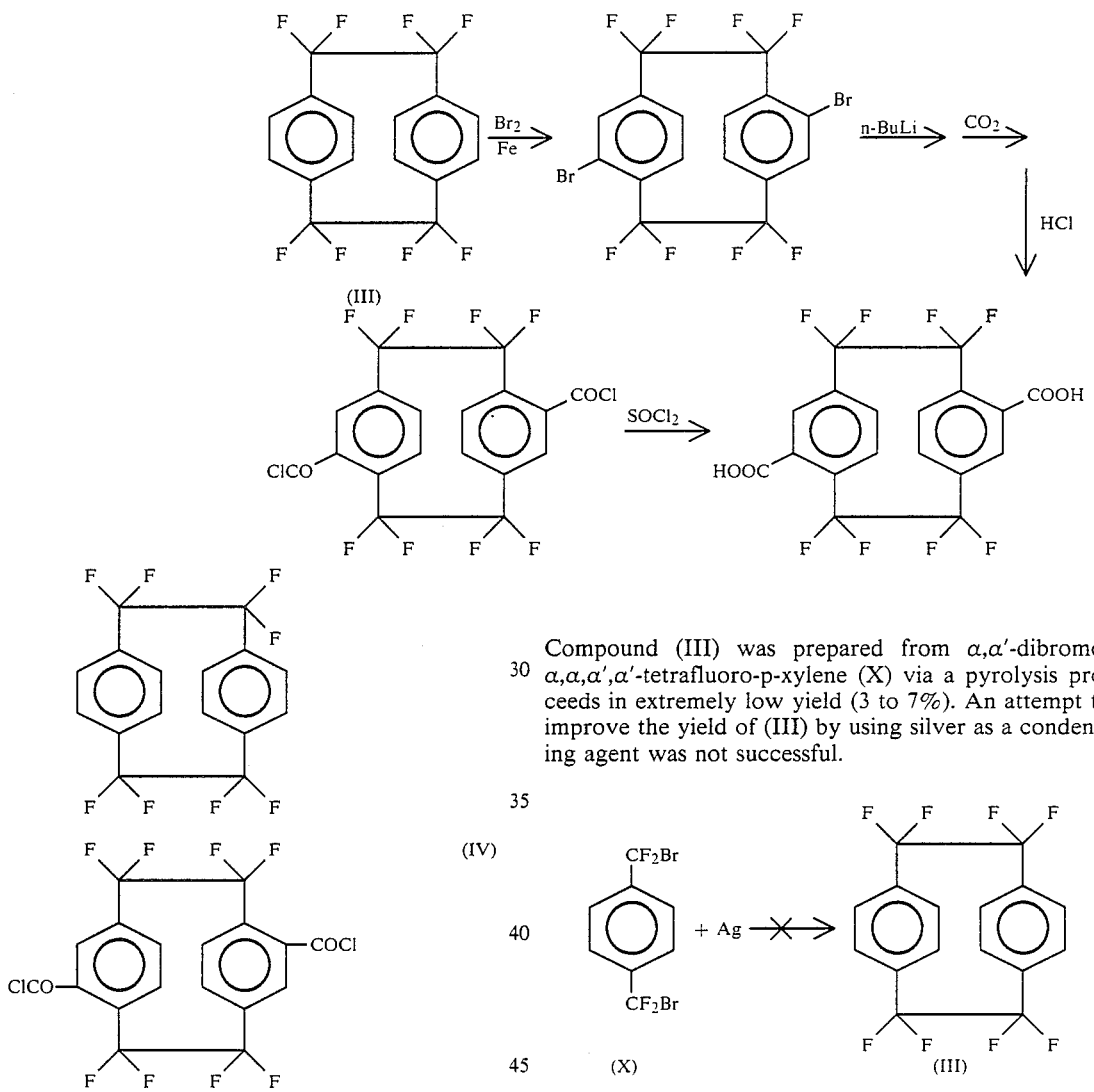

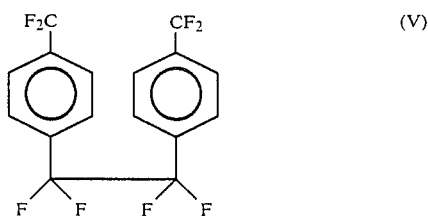

In comparison with structures (II), shown heretofore, the fluorine-substituted benzyl radicals of structure (V), shown below, are no doubt more stable and therefore can be prepared as homogenous laminates with greater thermal stability due to more complete cross-linking.

(V)

The monomer 1,1, 2,2, 9,9 10,10-octafluoro [2,2]-p-cyclophane (III) was prepared according to the procedure disclosed in R. A. Mayers et al, supra, while the other major monomer pseudo-p-1,1, 2,2, 9,9, 10,10-octafluoro [2,2]-p-cyclophane bis-acid chloride (IV) was synthesized from a reaction which uses monomer (III) as the starting material. This reactive is shown in Scheme I, follows.

Compound (III) was prepared from α,α'-dibromo-α,α,α',α'-tetrafluoro-p-xylene (X) via a pyrolysis proceeds in extremely low yield (3 to 7%). An attempt to improve the yield of (III) by using silver as a condensing agent was not successful.

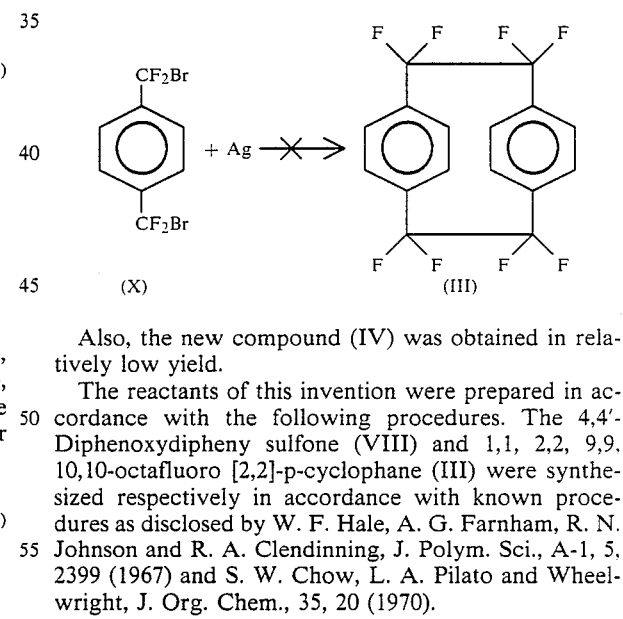

Also, the new compound (IV) was obtained in relatively low yield.

The reactants of this invention were prepared in accordance with the following procedures. The 4,4'-Diphenoxydipheny sulfone (VIII) and 1,1, 2,2, 9,9, 10,10-octafluoro [2,2]-p-cyclophane (III) were synthesized respectively in accordance with known procedures as disclosed by W. F. Hale, A. G. Farnham, R. N. Johnson and R. A. Clendinning, J. Polym. Sci., A-1, 5, 2399 (1967) and S. W. Chow, L. A. Pilato and Wheelwright, J. Org. Chem., 35, 20 (1970).

The pseudo-p-dibromo-1,1 2,2 9,9 10,10-octafluoro-[2,2]-p-cyclophane III monomer was prepared as shown in Example (I).

EXAMPLE I

A solution of 19 g (0.12 moles) of bromine in 160 ml of carbon tetrachloride was prepared and 12 ml of this solution was stirred with 0.2 g of iron filings and 200 ml of dichloromethane for 1 hr. The solution was brought to reflux, and 10 g (0.028 mores) of 1,1 2,2, 9,9, 10,10-octafluoro [2.2]-p-cyclophane was added. The remainder of the bromine solution was added over a period of 5 hr. Then the mixture was refluxed overnight. The solution was allowed to cool to room temperature, and washed with sodium bisulfite solution, and sodium chloride solution respectively. Then the solution was dried over anhydrous sodium sulfate. The solvent was removed on a rotary evaporator, and the crude product was recrystallized from chloroform to give a slightly yellow solid. 4.1 g m.p. 226°–235° C. NMR (CDCl$_3$): 7.28-7-7.31 (m) Anal. calcd. for C$_{16}$H$_6$Br$_2$F$_8$: C, 37.64%, H, 1.18%; Br, 31.37%; F, 29.80 Found: C, 37.12%; H, 1.05%; Br, 31.42%; F, 29.37.

The pseudo-p-dicarboxy-1,1 2,2, 9,9, 10,10-octafluoro [2,2]-p-cyclophane was prepared in accordance with the procedure of Example II.

EXAMPLE II

A mixture of 100 ml of dry ether and 5.1 g (0.01 moles) of pseudo-p-dibromo-1,1, 2,2, 9,9, 10,10-octafluoro [2,2]-p-cyclophane was stirred under nitrogen and 40 ml (an excess) of 1.6 N n-butyllithium in hexane was added in portions. The solution was stirred at −78° C. for 14 hr and at room temperature for an extra 8 hr. This solution was dumped into dry ice. After the reaction was completed and the dry ice evaporated, 150 ml of water was added and the aquesous layer was collected. Ether layer was washed with an additional 30 ml of water. The combined aqueous layer was neutralized with hydrochloric acid. The precipitated acid was filtered and washed with a large volume of water. The light yellow solid was dried under vacuum at 100° C. Yield: 2.3 g IR 1763 cm$^{-1}$(C)) m.p. above 300° C.

The novel pseudo-p-1,1, 2,2, 9,9, 10,10-octafluoro [2,2]-p-cyclophane bis acid chloride (IV) of this invention was prepared in accordance with the procedure of Example III.

EXAMPLE III

To a one-liter round-bottom three-necked flask, 5 g of pseudo-p-dicarboxy-1,1, 2,2, 9,9, 10,10-octafluoro [2,2]-p-cyclophane, 30 ml of thionyl cloride, 2 drops of DMF and 50 ml of dry benzene were added. The mixture was heated to reflux under nitrogen for 4 hr. After removal of extra thionyl chloride and benzene under an aspirator, the crude chloride was washed with hexane and recrystallized from n-hexane to give 3.6 g of light yellow solid. IR 1788 cm$_{-1}$ (CO) NMR (CDCl$_3$): 7.26–7.31 (m) m.p.: 205°–212° C. Anal. calcd. for C$_{18}$H$_6$Cl$_2$F$_8$O$_2$: C, 45.28%; H, 1.26%; Cl,14.88; F,31.85% Found C, 45.48%; H, 1.08%; Cl,14.32; F,31.34%

The isophthaloyl dichloride (V), terephthaloyl chloride (VII) and diphenyl ether (IX) were purified before use.

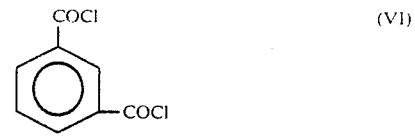

(VI)

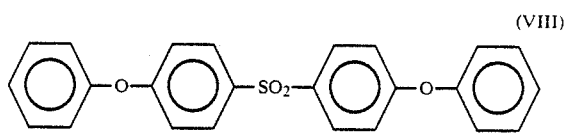

(VIII)

(VII)

(IX)

The novel polymeric materials prepared in accordance with this invention are of two types, hereinafter referred to as type A and type B. Specific polymers of both types are referred to in the following tables I and II as polymers A-1 to A-7 for type A and polymers B-1 to B-5 for Types B. These polymers were prepared with varying molar ratios under a mild reaction condition as shown in Table I. A-type polymers (containing monomer IV) are white powder, while B-type polymers are light yellow solid. The experimental data indicated that B-type polymers were of higher molecular weight. This could be due to the fact that monomer (IV) is not as reactive as (V), and therefore failed to give a complete reaction. The viscosities of these polymers were increased with increasing of mole ratio of terephthaloyl chloride, and decreased with increasing mole ratio of diphenyl ether. The solubility of polymers were decreased with increasing of mole ratio of terephthaloyl chloride and diphenyl ether. Most of these polymers can be prepared as strong, thin films and homogenous laminates. Their cured materials exhibited good thermal stability at 300° C. with weight losses below 4% after three days.

TABLE I

| Polymer | Monomer feed ratios | | | | | | Calculated (%) | | | | Found (%) | | | |
| --- | --- | --- | --- | --- | --- | --- | --- | --- | --- | --- | --- | --- | --- | --- |
| | III | IV | VI | VII | VIII | IX | C | H | S | F | C | H | S | F |
| A-1 | 1 | | 100 | | 99 | | 72.06 | 3.744 | 5.96 | 0.285 | 71.38 | 3.67 | 5.20 | — |
| A-2 | 1 | | 100 | | 80 | 19 | 72.97 | 3.77 | 5.25 | 0.311 | 69.65 | 3.90 | 4.86 | |
| A-3 | 10 | | 100 | | 80 | 10 | 71.46 | 3.610 | 5.08 | 3.06 | 70.64 | 4.10 | 4.67 | 1.82 |
| A-4 | 5 | | 100 | | 90 | 5 | 71.83 | 3.69 | 5.56 | 1.47 | 71.62 | 4.03 | 5.38 | — |
| A-5 | 5 | | 100 | | 95 | | 71.61 | 3.78 | 5.74 | 1.38 | 70.51 | 3.87 | — | — |
| A-6 | 5 | | 90 | 10 | 90 | 5 | 71.83 | 3.69 | 5.56 | 1.47 | 69.10 | 3.91 | — | — |
| A-7 | 5 | | 80 | 20 | 90 | 5 | 71.83 | 3.69 | 5.56 | 1.47 | 70.89 | 3.85 | 4.89 | 0.50 |
| B-1 | | 1 | 99 | | 100 | | 72.04 | 3.743 | 5.98 | 0.284 | 71.33 | 3.92 | — | — |
| B-2 | | 1 | 80 | 19 | 100 | | 72.04 | 3.743 | 5.98 | 0.284 | 71.08 | 3.84 | 5.41 | — |
| B-3 | | 10 | 90 | | 80 | 20 | 71.58 | 3.36 | 4.99 | 2.96 | 70.56 | 4.13 | 4.74 | 2.34 |
| B-4 | | 5 | 95 | | 100 | | 71.47 | 3.68 | 5.86 | 1.39 | 70.39 | 4.46 | 6.18 | — |
| B-5 | | 5 | 75 | 20 | 80 | 20 | 72.34 | 3.743 | 5.13 | 1.52 | 71.39 | 3.89 | 4.88 | 1.14 |

TABLE II

| Polymers | Softening temperature (°C.) | Solubility (in Ch$_2$Cl$_2$) | (in H$_2$SO$_4$) | n$_{inh}$ (%) | Weight loss |
| --- | --- | --- | --- | --- | --- |
| A-1 | 244–254 | | 5 | 0.472 | 3.4 |
| A-2 | 233–245 | | PS | 0.394 | — |
| A-3 | 238–249 | | PS | 0.433 | 1.8 |
| A-4 | 241–252 | | S | 0.512 | 2.3 |
| A-5 | 236–247 | | S | 0.542 | — |
| A-6 | 248–257 | | PS | 0.544 | — |
| A-7 | 252–263 | | PS | 0.576 | 2.1 |
| B-1 | 239–250 | | S | 0.483 | — |
| B-2 | 241–253 | | PS | 0.521 | 2.8 |
| B-3 | 238–251 | | PS | 0.472 | 1.6 |
| B-4 | 242–255 | | PS | 0.564 | — |
| B-5 | 246–260 | | PS | 0.583 | 2.0 |

Examples IV and V which follows illustrate the synthesis of the novel type A and Type B polyaromatic ether sulfone-ketones of this invention. Example IV discloses the synthesis of a polyaromatic ether-sulfone ketone with 1,1, 2,2, 9,9, 10,10-octafluoro[2,2]-p-cyclophane units and exemplifies the type B polymers shown in Tables I and II.

EXAMPLE IV

To a one-liter three-necked round-bottom flask (24/40) equipped with a condenser topped with nitrogen inlet, magnetic stirrer and addition funnel, exact amounts of isophthaloyl chloride (VI) and/or terephthaloyl chloride (VII) were dissolved in dry dichloromethane. The solution was cooled to 0° C. and anhydrous aluminum chloride (15% in excess) was added slowly. With stirring, a red solution was formed gradually. To the resulting red solution, theoretical molar quantities of 4,4'-diphenoxy-diphenyl (VIII) and/or diphenyl ether (IX) and 1,1, 2,2, 9,9, 10,10-octafluoro [2.2]-p-cyclophane (III) (in Ch$_2$Cl$_2$) were added dropwise. The mixture was stirred at 0° C. for 12 hr and at room temperature overnight. The polymer powder precipitated from the reaction mixture during polymerization. Precipitation was completed by adding ethanol. The precipitate was filtered off and washed several times with 95% ethanol in a blender. Yield: 73–86%. All of the polymers are white powders, most of them form strong films. The infrared spectra showed strong absorption at 1680 cm$^{-3}$.

Example V discloses the synthesis of a polyaromatic ether-sulfone-ketone with pseudo-p-1,1, 2,2, 9,9, 10,10-[2,2]-p-cyclophane bis-acid chloride units and exemplifies the type A polymers shown in Tables I and II.

EXAMPLE V

Using the same apparatus and procedure disclosed in Example IV, the exact amount of reactants (IV), (VI) and/or (VII) were placed in the flask. The complexes were generated in Ch$_2$Cl$_2$ at 0° C. for 6 hr and at room temperature overnight. Yield: 72–87%. Most of the polymers are light yellow powders. Most of them form strong films. The infrared spectra showed strong absorption at 1680cm$^{-1}$.

Thin films of the polymers of this invention were prepared by making saturated solutions in Ch$_2$Cl$_2$ and casting them on a watch glass to evaporate the solvent at room temperature. The polymer films were released from the glass by immersing them in water and drying in vacuo. The polymers were cured at 350° C. for three days and at 300° C. for two days under a load of 15,000 lbs in an aluminum foil. The aluminum foil was removed by reaction with hydrochloric acid.

Fiber glass laminates were prepared by placing the polymer (33 wt % to glass fiber) on a piece of glass fiber cloth, a few drops of DMF were added, and another piece of glass fiber cloth was put over and covered similarly with the polymer and a few drops of DMF. A third piece of cloth also covered the polymer. It was heated to 320° C. for two days under 20,000 lbs. in a Carver press. The polymers were also subjected to isothermal aging by being dried under high vacuum at 100° C. for three days. The present weight loss was determined by weighing the samples before and after the heat treatment.

The viscosities of polymers were determined on an Ubbelohde type viscometer in a thermal bath at 30° C. using sulfuric acid as solvent. MMR spectra were recorded on a Varian Em-390 spectrometer using CDCl$_3$ as solvent and Me$_4$Si as the internal standard. IR spectra were obtained on a Perkin-Elmer 337 spectrometer and calibrated against polystyrene. Elemental analyses were determined by the Analytical Center at the University of Arizona, MiCanal Organic Microanalysis, Tucson, Arizona and Micro-Tech Laboratories, Inc., Skokie, Illinois. Softening points were measured on a Thomas-Hoover melting-point apparatus.

From an examination of the foregoing, it will be seen that the present invention provides a new class of polyaromatic ether-sulfone-ketones which have been found to be especially useful when employed as laminating resins. These materials exhibit excellent thermal stability and strength after curing as well as good solubility before curing. The problems of forming voids in the finally cured polymer, a problem which occurred with prior art curing techniques due to the presence of gaseous side products, has been avoided also by practicing the present invention.

It should be understood by those skilled in the art to which the present invention pertains that while the compounds disclosed herein illustrate preferred embodiments of the invention, various modifications and alterations may be made without departing from the spirit and scope thereof, and that all such modifications as fall within the purview of the appended claims are intended to be included herein.

What is claimed:

1. A process for synthesizing a polyaromatic ether-sulfone-ketone containing fluoro-substituted-p-cyclophane units along the polymer chain which comprises the steps of (A) forming a reaction mixture of (1) isophthaloyl chloride and/or terephthaloyl chloride, (2) 2,2'-diphenoxy dyphenyl sulfone, (3) diphenyl ether, and (4) 1,1, 2,2, 9,9, 10,10-octafluoro [2,2]-p-cyclophane; (B) polymerizing said reaction mixture within a nitrogen atomsphere with stirring for a period of about 12 hours at 0° C. and then a period about 12 hours at room temperature; and (C) separating the resulting polymer.

2. The polymeric reaction product produced by the process of claim 1.

3. A process for synthesizing a polyaromatic ether-sulfone-ketone containing fluoro-substituted-p-cyclophane units along the polymer chain which comprises the steps of (A) forming a reaction mixture of (1) isophthaloyl chloride and/or terephthaloyl chloride, (2) 4,4'-diphenoxy diphenyl sulfone, (3) diphenyl ether, and (4) pseudo-p-1,1, 2,2, 9,9, 10,10-octafluoro[2,2]-p-cyclophane bis-acid chloride, (B) polymerizing said reaction product within a nitrogen atmosphere with stirring for a period of about 6 hours at 0° C. and then for a period of about 12 hours at room temperature; and (C) separating the resulting polymer.

4. The polymeric reaction product produced by the process of claim 1.

* * * * *